United States Patent [19]

Lesieur et al.

[11] Patent Number: 5,308,866

[45] Date of Patent: May 3, 1994

[54] BENZOFURAN ETHYLAMINE COMPOUNDS

[75] Inventors: Daniel Lesieur, Gondecourt; Said Yous, Lille; Patrick Depreux, Armentieres; Jean Andrieux, Antony; Gérard Adam, Le Mesnil Le Roi; Daniel H. Caignard, Paris; Béatrice Guardiola, Neuilly Sur Seine, all of France

[73] Assignee: Adir et Compagnie, Courbevoie, France

[21] Appl. No.: 93,279

[22] Filed: Jul. 19, 1993

Related U.S. Application Data

[62] Division of Ser. No. 931,574, Aug. 12, 1992.

[30] Foreign Application Priority Data

Aug. 13, 1991 [FR] France .............................. 91 10261

[51] Int. Cl.$^5$ ..................... A61K 31/34; C07D 307/81
[52] U.S. Cl. .................................... 514/469; 514/470; 549/466; 549/467
[58] Field of Search ................ 549/466, 467; 514/469, 514/470

[56] References Cited

U.S. PATENT DOCUMENTS 4,243,668  1/1981  Ciganek .............................. 546/66
4,663,347  5/1987  Atkinson et al. .................... 514/467

*Primary Examiner*—Joseph Paul Brust
*Assistant Examiner*—Mary Susan H. Gabilan
*Attorney, Agent, or Firm*—Gordon W. Hueschen

[57] ABSTRACT

The invention relates to a compound selected from those of formula (I):

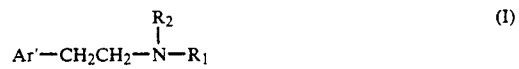

in which Ar', $R_1$ and $R_2$ are as defined in the specification,
an optical isomer,
and an addition salt thereof with a pharmaceutically-acceptable acid or base.
Medicinal product which is useful in treating or in preventing a disorder of the melatoninergic system.

5 Claims, No Drawings

BENZOFURAN ETHYLAMINE COMPOUNDS

The present application is a division of our prior-filed copending application Ser. No. 07/931,574, filed Aug. 12, 1992.

The present invention relates to new arylethylamine compounds, to processes for the preparation thereof, and to pharmaceutical compositions containing them.

A certain number of arylethylamine compounds having an indole nucleus are described as being agonists or antagonists of melatonin, both in patents GB 219 2001 and WO 89/01472, and in the publications J. Med. Chem. (1979) 22 (1) pp. 63–69 and Chemical Abstract (1968) 70 (1) no. 3722 T.

The same applies to a number of compounds having a benzo[b]thiophene nucleus: J. Med. Chem. (1970) 13 pp. 1205–1208, J. Heterocyclic Chem. (1978) 15 pp. 1351–1359, (1983) 20 pp. 1697–1703.

Benzo[b]furan analogues of melatonin have likewise been synthesised: Annalen (1963) 662 pp. 147–159 and patent FR 1343073, but no pharmacological activity of the melatoninomimetic type appears to have been found.

The same applies in the benzimidazole series, where demethoxylated analogues of melatonin have been prepared without such activity appearing to have been found: Khimiko Farmatsevticheskii Zhurnal (1968) 9 pp. 21–23.

The Applicant has now found new compounds having an affinity for the melatonin receptors that is very considerably superior to that of the products described in the literature and to that of melatonin itself.

Those compounds possess numerous valuable pharmacological activities on account of their agonistic or antagonistic nature towards melatonin.

In addition to their beneficial action on disturbances in the circadian rhythm and sleep disorders and on seasonal disorders, they have valuable pharmacological properties on the central nervous system, especially anxiolytic, antipsychotic and analgesic properties, and on ovulation, cerebral circulation and immunomodulation.

More specifically, the present invention relates to the compounds of the general formula (I):

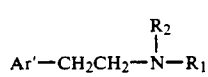

(I)

in which:
Ar' represents:
an indol-3-yl nucleus of formula (II):

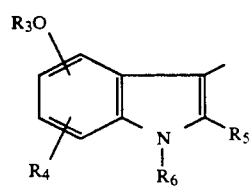

(II)

a benzo[b]thiophen-3-yl nucleus of formula (III):

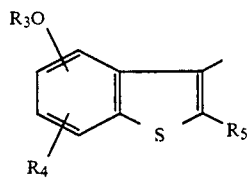

(III)

a benzimidazol-1-yl nucleus of formula (IV):

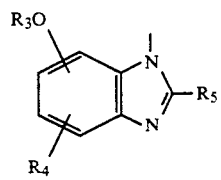

(IV)

a benzo[b]furan-3-yl nucleus of formula (V):

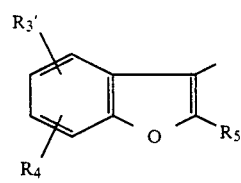

(V)

a 1,2-benzisoxazol-3-yl nucleus of formula (VI):

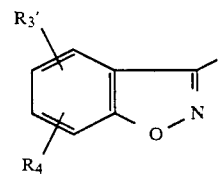

(VI)

a 1,2-benzisothiazol-3-yl nucleus of formula (VII):

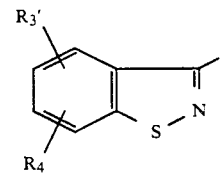

(VII)

an indazol-3-yl nucleus of formula (VIII):

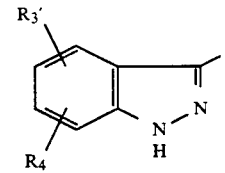

(VIII)

$R_1$ represents:
a group

in which $R_7$ represents an optionally substituted cycloalkyl radical, an optionally substituted cycloalkyl-($C_1$-$C_4$)alkyl radical, or a trifluoromethyl group, and, when Ar' represents a group selected from those of formulae (IV), (VI), (VII) and (VIII), $R_7$ may also represents a linear or branched alkyl radical having from 1 to 6 carbon atoms that is unsubstituted or substituted by 1 or 2 halogen radicals, group

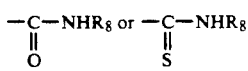

in which $R_8$ represents a linear or branched lower alkyl radical having from 1 to 6 carbon atoms, an optionally substituted cycloalkyl radical, an optionally substituted cycloalkyl-($C_1$-$C_4$-)alkyl radical, an optionally substituted aryl radical, or an optionally substituted arylalkyl radical the alkyl chain of which contains from 1 to 3 carbon atoms,
or
a group

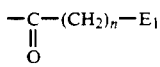

in which n represents an integer from I to 3 and $E_1$ represents a radical selected from:
morpholino and
piperazine that is unsubstituted or substituted by a radical -$(CH_2)_{n'}$-$E_2$ wherein n' represents an integer from 1 to 4 and $E_2$ represents a phenyl or naphthyl radical each of which is unsubstituted or substituted by from 1 to 3 radicals selected from: halogen, ($C_1$-$C_4$)alkyl and ($C_1$-$C_4$)alkoxy;
$R_2$ represents a hydrogen atom or a linear or branched lower alkyl radical having from 1 to 6 carbon atoms;
$R_3$ represents a hydrogen atom, a linear or branched lower alkyl radical having from 1 to 6 carbon atoms, an optionally substituted aryl radical, an optionally substituted arylalkyl or diarylalkyl radical in which the alkyl chain contains from 1 to 3 carbon atoms, or a cycloalkyl or cycloalkylalkyl radical in which the alkyl chain contains from 1 to 3 carbon atoms;
$R_3'$ represents a hydrogen atom or a group —O—$R_3$ wherein $R_3$ is as defined above;
$R_4$ represents a hydrogen atom, a halogen atom, a hydroxy radical, a linear or branched alkoxy radical having from 1 to 6 carbon atoms, or a linear or branched lower alkyl radical having from 1 to 6 carbon atoms;
$R_5$ represents a hydrogen atom, a halogen atom, a linear or branched lower alkyl radical having from 1 to 6 carbon atoms, an optionally substituted phenyl radical, or an optionally substituted phenylalkyl radical in which the alkyl chain contains from 1 to 3 carbon atoms; and
$R_6$ represents a hydrogen atom, or a linear or branched lower alkyl radical having from 1 to 6 carbon atoms;
the isomers, epimers and diastereoisomers thereof, and the addition salts thereof with a pharmaceutically acceptable acid or base,
with the provisos that:

Ar' may not represent a 7-methoxybenzo[b]furan-3-yl group when $R_1$ represents a cyclopropylcarbonyl radical;
$R_1$ may not represent a trifluoroacetyl radical when Ar' represents an indole radical wherein $R_2$ =$R_3$=$R_4$=$R_5$=$R_6$=H;
and $R_1$ may not represent an anilinothiocarbonyl radical that is unsubstituted or substituted at the 4-position of the phenyl by an alkoxy radical, when Ar represents an indol-3-yl nucleus and $R_3$ represents a methyl or benzyl radical;
and wherein
the term "substituted" associated with the expressions "aryl", "arylalkyl", "diarylalkyl", "phenyl" and "phenylalkyl" indicates that the aromatic nucleus or nuclei may be substituted by one or more radicals selected from: linear or branched lower alkyl having from 1 to 6 carbon atoms, linear or branched lower alkoxy having from 1 to 6 carbon atoms, hydroxy, halogen, nitro, and trifluoromethyl;
the term "substituted" associated with the expressions "cycloalkyl" and "cycloalkyl-($C_1$-$C_4$)alkyl" indicates that the cyclic system may be substituted by one or more radicals selected from: halogen, linear or branched lower alkyl having from 1 to 6 carbon atoms, and linear or branched lower alkoxy having from 1 to 6 carbon atoms;
the term "cycloalkyl" designates a saturated or unsaturated cyclic system having from 3 to 8 carbon atoms; and
the expression "aryl group" is understood as meaning a pyridyl, phenyl, naphthyl, thienyl, furyl or pyrimidyl group.

The present invention relates also to a process for the preparation of the compounds of formula (I), characterised in that there is used as starting material an amine of the general formula (IX):

in which Ar' and $R_2$ have the same meaning as in formula (I), which is treated:
with an acid chloride of formula (X):

or with the corresponding acid anhydride of formula (XI):

in which formulae $R_7$ has the same meaning as in formula (I), to obtain the compounds of formula (Ia):

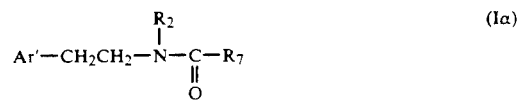

in which Ar', $R_2$ and $R_7$ have the same meaning as in formula (I),
or with an isocyanate of formula (XII):

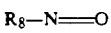 (XII), in which $R_8$ has the same meaning as in formula (I), to obtain the compounds of formula (Iβ):

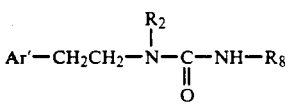 (Iβ)

in which Ar', $R_2$ and $R_8$ have the same meaning as in formula (I),
or with an isothiocyanate of formula (XIII):

 (XIII), in which $R_8$ has the same meaning as in formula (I), to obtain the compounds of formula (Iγ):

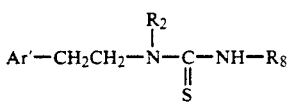 (Iγ)

in which Ar', $R_2$ and $R_8$ have the same meaning as in formula (I), it being understood that the compounds of formulae (Iα), (Iβ) and (Iγ) form part of the invention and together constitute the compounds of formula (I), it being possible for the compounds of formula (I) to be:
  purified by one or more purification methods selected from crystallisation, chromatography over a silica column, extraction, filtration, and passage over carbon and/or resin,
  separated, where applicable, in pure form or in the form of a mixture, into their possible optical isomers,
  and/or converted into salts by means of a pharmaceutically acceptable acid or base.

The invention also includes a process for obtaining the compounds of formula ($I_{68}$):

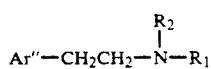 (Iε)

in which $R_1$ and $R_2$ are as defined in formula (I) and Ar'' represents a group Ar' as defined in formula (I) that is substituted by a group —O—$R_3''$ wherein $R_3''$ represents a group selected from optionally substituted aryl, optionally substituted arylalkyl or diarylalkyl, and cycloalkyl or cycloalkylalkyl (the terms "aryl", "arylalkyl", "diarylalkyl", "cycloalkyl", "cycloalkylalkyl" and "substituted" being as defined in formula (I)), characterised in that a compound of formula ($I_{68}$'):

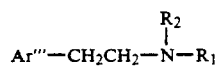 (Iε')

in which $R_1$ and $R_2$ are as defined above and Ar''' represents a group Ar' as defined in formula (I) that is substituted by a group —O—$R_3'''$ wherein $R_3'''$ represents a hydrogen atom, is reacted with a compound of formula (XIV):

 (XIV)

in which Hal represents a halogen atom and R'' represents a group selected from optionally substituted aryl, optionally substituted arylalkyl or diarylalkyl, and cycloalkyl or cycloalkylalkyl (the terms "aryl", "arylalkyl", "diarylalkyl", "cycloalkyl", "cycloalkylalkyl" and "substituted" being as defined in formula (I)), it being possible for the compounds of formula ($I_{68}$) to be:
  purified by one or more purification methods selected from crystallisation, chromatography over a silica column, extraction, filtration, and passage over carbon and/or resin,
  separated, where applicable, in pure form or in the form of a mixture, into their possible optical isomers,
  and/or converted into salts by means of a pharmaceutically acceptable acid or base.

The invention also includes a process for the preparation of the compounds of formula (Iφ):

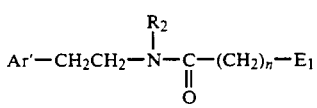 (Iφ)

in which Ar', $R_2$, $E_1$ and n are as defined in formula (I), characterised in that a compound of formula (Iφ'):

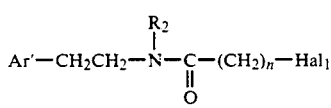 (Iφ')

in which Ar', $R_2$ and n are as defined in formula (I) and $Hal_1$ represents a halogen atom, is reacted with a morpholine group or with a piperazine group that is unsubstituted or substituted by a radical —$(CH_2)_{n'}$—$E_2$ wherein n' and $E_2$ are as defined in formula (I), it being possible for the compounds of formula (Iφ) to be:
  purified by one or more purification methods selected from crystallisation, chromatography over a silica column, extraction, filtration, and passage over carbon and/or resin,
  separated, where applicable, in pure form or in the form of a mixture, into their possible optical isomers,
  and/or converted into salts by means of a pharmaceutically acceptable acid or base.

The amines of formula (IX) are either commercially available or readily accessible to the person skilled in the art.

The compounds of formula (I) have valuable pharmacological properties.

The pharmacological study of those compounds has in fact shown that they have low toxicity and a very high selective affinity for the melatonin receptors (which is far superior to that of melatonin itself and to that of its analogues described in the literature).

Among their important activities on the central nervous system, the compounds of the invention have sedative, anxiolytic, anti-psychotic and analgesic properties as well as properties affecting microcirculation, as a result of which they can be used in the treatment of stress, of sleep disorders, of anxiety, of seasonal depression, of insomnia and fatigue due to jet lag, of schizophrenia, of panic attacks, of melancholia, of regulation of the appetite, of insomnia, of psychotic disorders, of epilepsy, of Parkinson's disease, of senile dementia, of disorders associated with normal or pathological ageing, of migraine, of memory loss, of Alzheimer's disease and of disorders of cerebral circulation.

The compounds of the invention also have ovulation-inhibiting and immunomodulatory properties, which enable them to be used in the treatment of certain cancers.

When administered externally, they may be used in the treatment of psoriasis, of acne and of seborrhoea, and they protect the skin.

They may also be used in veterinary medicine for their properties on the fur.

The present invention relates also to pharmaceutical compositions containing the products of formula (I) on their own or in combination with one or more inert, non-toxic, pharmaceutically acceptable excipients or vehicles.

Of the pharmaceutical compositions according to the invention there may be mentioned, by way of non-limiting examples, those which are suitable for oral, parenteral, nasal, per- or transcutaneous, rectal, perlingual, ocular or respiratory administration, and especially tablets, dragees, sublingual tablets, sachets, paquets, gelatin capsules, glossettes, lozenges, suppositories, creams, ointments, dermic gels, and injectable and drinkable ampoules.

The dosage varies according to the age and weight of the patient, the mode of administration and the nature of the therapeutic indication or of any associated treatments, and ranges from 0.1 mg to 1 g per 24 hours.

The following Examples illustrate the invention but do not limit it in any way.

EXAMPLE 1: N-[2-(5-METHOXYINDOL-3-YL)ETHYL]-CYCLOPROPYLCARBOXAMIDE 3 g of 5-methoxytryptamine are added to a solution of 2.2 g of potassium carbonate in 40 cm³ of water. 80 cm³ of chloroform are added, and then 1.7 g of cyclopropanecarboxylic acid chloride are added with very vigorous stirring. After stirring at room temperature for 30 minutes, the organic phase is separated off, washed with water and then dried.

The resulting residue is crystallised in toluene, yielding 3.3 g (80.5%) of N-[2-(5-methoxyindol-3-yl)ethyl]-cyclopropylcarboxamide.

Melting point: 101°-102° C.

Infra-red (KBr disc): 3390 cm⁻¹ ν NH indole; 3250-3300 cm⁻¹ ν NH amide; 2900-3050 cm⁻¹ ν CH alkyl; 1630 cm⁻¹ ν CO amide;

¹H-NMR 80 MHz (CDCl₃)

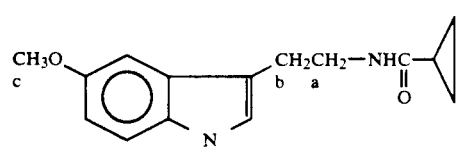

| | | |
|---|---|---|
| 0.7-1 ppm | (5H) | cyclopropyl |
| 2.8-3 ppm | (2H) | CH₂ b |
| 3.4-3.7 ppm | (2H) | CH₂ a |
| 3.8 ppm | (H) | OCH₃ |
| 6.7-7.3 ppm | (4H) | indole |
| 8.1 ppm | (1H) | NH (indole) |

EXAMPLE 2: N-[2-(6 FLUORO 5-METHOXYINDOL 3-YL)ETHYL]-CYCLOPROPYLCARBOXAMIDE

Following the procedure of Example 1 but replacing 5-methoxytryptamine with 5-methoxy-6-fluorotryptamine (J. Heterocyclic Chem. (1976) 13 pp. 1253-1256), N-[2-(5-methoxy-6-fluoroindol-3-yl)ethyl]-cyclopropylcarboxamide is obtained. Melting point (dichloromethane-ether): 125°-126° C.

EXAMPLE 3: N-[2-(6-CHLORO-5 METHOXYINDOL-3-YL)ETHYL]-CYCLOPROPYLCARBOXAMIDE

Following the procedure of Example 1 but replacing 5-methoxytryptamine with 5-methoxy-6-chlorotryptamine (Synthesis (1983) pp. 935-936), N-[2-(5-methoxy-6-chloroindol-3-yl)ethyl]-cyclopropylcarboxamide is obtained.

EXAMPLE 4: N-[2-(5-METHOXY-2,6-DIMETHYLINDOL-3-YL)ETHYL]-CYCLOPROPYLCARBOXAMIDE

Following the procedure of Example 1 but replacing 5-methoxytryptamine with 5-methoxy-2,6-dimethyltryptamine (Journal of Medicinal Chemistry (1973) 16 pp. 757-765), N-[2-(5-methoxy-2,6-dimethylindol-3-yl)ethyl]-cyclopropylcarboxamide is obtained.

EXAMPLE 5: N-[2-(5-METHOXYBENZO[b]THIOPHEN-3-YL)ETHYL]-CYCLOPROPYLCARBOXAMIDE

Following the procedure of Example 1 but replacing 5-methoxytryptamine with 3-β-aminoethyl-5-methoxybenzo[b]thiophene (Journal of Medicinal Chemistry (1970) 13 pp. 1205-1208), N-[2-(5-methoxybenzo[b]thiophen-3-yl)ethyl]-cyclopropylcarboxamide is obtained.

Melting point : 124°-126° C.

Infra-red (KBr disc): 3270cm⁻¹ ν NH amide; 1640 cm⁻¹ ν CO amide.

EXAMPLE 6: N-[2-(6-CHLORO-5-METHOXYBENZO[b]THIOPHEN-3-YL)ETHYL]-CYCLOPROPYLCARBOXAMIDE

Following the procedure of Example 1 but replacing 5-methoxytryptamine with 3-β-aminoethyl-5-methoxy-6-chlorobenzo[b]thiophene (J. Heterocyclic Chem. (1983) 20 pp. 1671-1703), N-[2-(5-methoxy-6-chlorobenzo[b]thiophen-3-yl) ethyl]-cyclopropylcarboxamide is obtained.

EXAMPLE 7 N [2-(5 METHOXYBENZO[b]FURAN-3-YL)ETHYL]-CYCLOPROPYLCARBOXAMIDE

Following the procedure of Example 1 but replacing 5-methoxytryptamine with 3-β-aminoethyl-5-methoxybenzo[b]furan (Annalen (1963) 662 pp. 147-159 or Aust. J. Chem. (1975) 28 pp. 1097-111-1), N-[2-(5-methoxybenzo[b]furan-3-yl)ethyl]-cyclopropylcarboxamide is obtained.

Infra-red (KBr disc): 3290 cm⁻¹ ν NH amide; 1680 cm⁻¹ ν C=O amide.

¹H-NMR 80 MHz (CDCl₃)

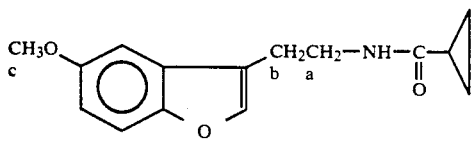

| 0.7–1 ppm | (5H) | cyclopropyl |
|---|---|---|
| 2.9 ppm | (2H) | CH₂ b |
| 3.5–3.7 ppm | (2H) | CH₂ a |
| 3.9 ppm | (3H) | OCH₃ |
| 6.8–7.3 ppm | (4H) | benzo[b]furan |

EXAMPLE 8: N [2-(2-METHYL 5-METHOXYBENZO[b]FURAN-3-YL)-ETHYL]-CYCLOPROPYLCARBOXAMIDE

Following the procedure of Example 1 but replacing 5-methoxytryptamine with 2-methyl-3-β-aminoethyl-5-methoxybenzo[b]furan (Patent FR 1343073), N-[2-(2-methyl-5-methoxybenzo[b]furan-3-yl)ethyl]-cyclopropylcarboxamide is obtained.

Infra-red (KBr disc): 3320 cm⁻¹ ν NH amide; 1650 cm⁻¹ ν CO amide.

EXAMPLE 9: N-2-(6-METHOXYBENZIMIDAZOL-1 YL)ETHYL]-CYCLOPROPYLCARBOXAMIDE

Following the procedure of Example 1 but replacing 5-methoxytryptamine with 1-β-aminoethyl-6-methoxybenzimidazole (J. Chem. Soc. (1957) pp. 1671–1674), N-[2-(6-methoxybenzimidazol-1-yl)ethyl]-cyclopropylcarboxamide is obtained.

Melting point (Ethyl acetate) : 86°–88° C.

Infra-red (KBr disc): 3300 cm⁻¹ ν NH amide, 1660 cm⁻¹ ν CO amide.

EXAMPLE 10: N [2 (2-BENZYL-6-METHOXYBENZIMIDAZOL-1-YL)-ETHYL]-CYCLOPROPYLCARBOXAMIDE

Following the procedure of Example 1 but replacing 5-methoxytryptamine with 1-β-aminoethyl-2-benzyl-6-methoxybenzimidazole (Patent FR 2182915), N-[2-(2-benzyl-6-methoxybenzimidazol-1-yl)ethyl]-cyclopropylcarboxamide is obtained.

EXAMPLE 11: N [2 (5-METHOXY-1,2-BENZISOXAZOL-3-YL)ETHYL]-CYCLOPROPYLCARBOXAMIDE

Following the procedure of Example 1 but replacing 5methoxytryptamine with 3-β-aminoethyl-5-methoxy-1,2-benzisoxazole (Chem. Pharm. Bull. (1976) 24 (4)pp. 632–643), N-[2-(5-methoxy-1,2-benzisoxazol-3-yl)ethyl]-cyclopropylcarboxamide is obtained.

EXAMPLE 12: N-[2-(5 METHOXY-1,2-INDAZOL-3-YL)ETHYL]-CYCLOPROPYLCARBOXAMIDE

Following the procedure of Example 1 but replacing 5-methoxytryptamine with 3-β-aminoethyl-5-methoxyindazole (J.A.C.S. (1957) 79 pp. 5245–5247), N-[2-(5-methoxy-1,2-indazol-3-yl)ethyl]-cyclopropylcarboxamide is obtained.

EXAMPLE 13: N-[2 (5-METHOXYINDOL 3-YL)ETHYL]-TRIFLUOROACETAMIDE 1.14 g of trifluoroacetic acid are added dropwise to a suspension, at −5° C., of 1.90 g of 5-methoxytryptamine in 6 cm³ of pyridine. The mixture is stirred at room temperature for 30 minutes and then the reaction medium is poured onto icewater. The resulting precipitate is isolated by filtration, washed with water, dried and then recrystallised in toluene.

1.14 g (40%) of N-[2-(5-methoxyindol-3-yl)ethyl]-trifluoroacetamide are obtained.

Melting point: 135°–136° C.

Infra-red (KBr disc): 3400 cm⁻¹ ν NH indole; 3300 cm⁻¹ ν NH amide; 1700 cm⁻¹ ν C=O.

¹H-NMR 80 MHz (CDCl₃)

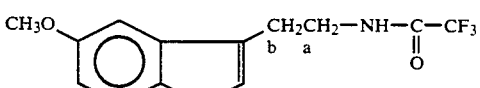

| 3 ppm | (2H) | CH₂ b |
|---|---|---|
| 3.6 ppm | (2H) | CH₂ a |
| 3.8 ppm | (3H) | OCH₃ |
| 6.8–7.3 ppm | | aromatic protons |

EXAMPLE 14: N-[2-(5-METHOXYBENZO[b]THIOPHEN-3-YL)ETHYL]-TRIFLUOROACETAMIDE

Following the procedure of Example 13 but replacing 5-methoxytryptamine with 3-β-aminoethyl-5-methoxybenzo[b]thiophene, N-[2-(5-methoxybenzo[b]thiophen-3-yl)ethyl]-trifluoroacetamide is obtained.

Infra-red (KBr disc): 3280 cm⁻¹ ν NH amide; 1690 cm⁻¹ ν C=O.

EXAMPLE 15: N-[2-(5-METHOXYBENZO[b]FURAN-3-YL)ETHYL]-TRIFLUOROACETAMIDE

Following the procedure of Example 13 but replacing 5-methoxytryptamine with 3-β-aminoethyl-5-methoxybenzo[b]furan, N-[2-(5-methoxybenzo[b]furan-3-yl)ethyl]-trifluoroacetamide is obtained.

Infra-red (KBr disc): 3290 cm⁻¹ ν NH amide; 1700 cm⁻¹ ν C=O amide.

EXAMPLE 16: N [2-(6-METHOXYBENZIMIDAZOL-1-YL)ETHYL]-TRIFLUOROACETAMIDE

Following the procedure of Example 13 but replacing 5-methoxytryptamine with 1-β-aminoethyl-6-methoxybenzimidazole, N-[2-(6-methoxybenzimidazol-1-yl)ethyl]-trifluoroacetamide is obtained.

Infra-red (KBr disc): 3300 cm⁻¹ ν NH amide 1690 cm⁻¹ ν C=O amide.

EXAMPLE 17: N-[2-(5 METHOXY-1,2 BENZISOXAZOL-3-YL)ETHYL]-TRIFLUOROACETAMIDE

Following the procedure of Example 13 but replacing 5-methoxytryptamine with 3-β-aminoethyl-5-methoxy-1,2-benzisoxazole, N-[2-(5-methoxy-1,2-benzisoxazol-3-yl)ethyl]trifluoroacetamide is obtained.

EXAMPLE 18: N-[2-(5-METHOXYINDOL-3-YL)ETHYL]-N'-PROPYLUREA 0.851 g of propyl isocyanate is added to a suspension of 1.902 g of 5-methoxytryptamine in 4 cm$^3$ of pyridine at +5° C. The mixture is stirred at room temperature for 2 hours and then the reaction medium is poured onto ice-water. The mixture is acidified slightly with a 1N hydrochloric acid solution. The resulting precipitate is isolated by filtration, washed with water, dried and then recrystallised in toluene, yielding 2.34 g (85%) of N-[2-(5-methoxyindol-3-yl)ethyl]-N'-propylurea.

Melting point: 79°-80° C.

$^1$H-NMR 80 MHz (CDCl$_3$)

CH$_3$O—[indole ring]—CH$_2$CH$_2$NHCNHCH$_2$CH$_2$CH$_3$
  a   b   ‖   c   d   e
              O

| | | |
|---|---|---|
| 0.9 ppm | (3H) | CH$_3$ e |
| 1.4 ppm | (2H) | CH$_2$ d |
| 2.9 ppm | (4H) | CH$_2$ a CH$_2$ c |
| 3.4 ppm | (2H) | CH$_2$ b |
| 3.9 ppm | (3H) | OCH$_3$ |
| 6.6–7.3 ppm | | aromatic protons |

EXAMPLE 19: N-[2 (5-METHOXYBENZO[b]THIOPHEN-3 YL)ETHYL]-N'-PROPYLUREA

Following the procedure of Example 18 but replacing 5-methoxytryptamine with 3-β-aminoethyl-5-methoxybenzo [b]thiophene, N-[2-(5-methoxybenzo[b]thiophen-3-yl)ethyl]-N'-propylurea is obtained.

Infra-red (KBr disc): 3300 cm$^{-1}$ v NH; 1620 cm$^{-1}$ v C=O.

EXAMPLE 20: N [2-(6-CHLORO-5 METHOXYINDOL 3-YL)ETHYL]-N'-PROPYLUREA

Following the procedure of Example 18 but replacing 5-methoxytryptamine with 5-methoxy-6-chlorotryptamine, N-[2-(5-methoxy-6-chloroindol-3-yl)ethyl]-N'-propylurea is obtained.

Infra-red (KBr disc): 3250 cm$^{-1}$ v NH; 1620 cm$^{-1}$ v C=O.

$^1$H-NMR 80 MHz (CDCl$_3$)

CH$_3$O—[indole ring, Cl]—CH$_2$CH$_2$NHCNHCH$_2$CH$_2$CH$_3$
  a   b   ‖   c   d   e
              O

| | | |
|---|---|---|
| 0.9–1 ppm | (3H) | CH$_3$ e |
| 1.5 ppm | (2H) | CH$_2$ d |
| 2.8–3 ppm | (4H) | CH$_2$ b CH$_2$ c |
| 3.4 ppm | (2H) | CH$_2$ a |
| 3.90 ppm | (3H) | OCH$_3$ |

EXAMPLE 21: N [2 (5-METHOXYBENZO[b]FURAN-3-YL)ETHYL]-N'-PROPYLUREA

Following the procedure of Example 18 but replacing 5-methoxytryptamine with 3-β-aminoethyl-5-methoxybenzo[b]furan, N-[2-(5-methoxybenzo[b]furan-3-yl)ethyl]-N'-propylurea is obtained.

Infra-red (KBr disc): 3290 cm$^{-1}$ v NH; 1620 cm$^{-1}$ v C=O.

EXAMPLE 22: N [2-(5 METHOXYINDOL-3-YL)ETHYL]-N'-PROPYL-THIOUREA 1.11 g of propyl isothiocyanate are added to a suspension of 2.27 g of 5-methoxytryptamine in 5 cm$^3$ of pyridine.

The reaction medium is stirred at 80° for one hour and then, after cooling, is poured onto a mixture of water and ice and acidified slightly with a 1N hydrochloric acid solution.

The resulting precipitate is isolated by filtration, washed with water, dried and then recrystallised in toluene. In this manner, 2.18 g (75%) of N-[2-(5-methoxyindol-3-yl)ethyl]-N'-propylthiourea are obtained. $^1$H-NMR 80 MHz (CDCl$_3$)

CH$_3$O—[indole ring]—CH$_2$CH$_2$—NH—C—NH—CH$_2$CH$_2$CH$_3$
  a   b   ‖   c   d   e
              S

| | | |
|---|---|---|
| 0.85 ppm | (3H) | CH$_3$ e |
| 1.45 ppm | (2H) | CH$_2$ d |
| 2.95 ppm | (4H) | CH$_2$ c CH$_2$ a |
| 3.4 ppm | (2H) | CH$_2$ b |
| 3.85 ppm | (3H) | OCH$_3$ |
| 5.50 ppm | (2H) | HNCNH disappears in D$_2$O<br>‖<br>S |
| 6.7–7.3 ppm | | aromatic protons |

EXAMPLE 23: N-[2-(5-METHOXYINDOL-3-YL)ETHYL]-CYCLOBUTYLCARBOXAMIDE

Following the procedure of Example 1 but replacing cyclopropanecarboxylic acid chloride with cyclobutanecarboxylic acid chloride, the title compound is obtained.

Melting point: 111°-112° C.

Crystallisation solvent: chloroform-acetone.

EXAMPLES 24 TO 25

Following the procedure of Example 1 but replacing cyclopropanecarboxylic acid chloride with the appropriate acid chloride or, where applicable, its corresponding acid anhydride, the compounds of the following Examples are obtained:

EXAMPLE 24: N-[2-(5-METHOXYINDOL-3-YL)ETHYL]-CYCLOHEXYLCARBOXAMIDE

EXAMPLE 25: N-[2-(5-METHOXYINDOL-3-YL)ETHYL]-3-CYCLOPENTYLPROPIONAMIDE

EXAMPLE 26: N-[2-(5-METHOXYINDOL-3-YL)ETHYL]-MORPHOLINOACETAMIDE

Step I: N-[2-(5-METHOXYINDOL-3-YL)ETHYL]-BROMOACETAMIDE

Following the procedure of Example 1 but replacing cyclopropanecarboxylic acid chloride with bromoacetic acid chloride, N-[2-(5-methoxyindol-3-yl)ethyl]-bromoacetamide is obtained.

Step II: N-[2-(5-METHOXYINDOL-3-YL)ETHYL]-MORPHOLINOACETAMIDE 0.01 mol of morpholine is dissolved in 50 cm³ of acetone, with magnetic stirring. 0.012 mol of triethylamine and 0.01 mol of N-[2-(5-methoxyindol-3-yl)ethyl]-2-bromoacetamide are added. The mixture is refluxed for one hour with magnetic stirring. The resulting precipitate is suction filtered and the filtrate is evaporated.

The residue is taken up in alkaline water, and the precipitate is suction filtered, washed, dried and recrystallised in a toluene-cyclohexane mixture, yielding the title compound.

EXAMPLES 27 AND 28

Following the procedure of Example 26 but replacing morpholine in step II with 1-benzylpiperazine and then with 1-(2,3,4-trimethoxybenzyl)piperazine, the compounds of the following Examples are obtained in succession:

EXAMPLE 27: N-[2-(5 METHOXYINDOL 3-YL)ETHYL]-2-(4-BENZYLPIPERAZIN-1-YL)ACETAMIDE

EXAMPLE 28: N-[2 (5 METHOXYINDOL-3-YL)ETHYL]-2-(4-(2,3,4-TRIMETHOXYBENZYL)PIPERAZIN-1 YL)ACETAMIDE

EXAMPLE 29: N-[2-(5-HYDROXYINDOL-3-YL)ETHYL]-CYCLOPROPYLCARBOXAMIDE

Following the procedure of Example 1 but replacing 5-methoxytryptamine with 5-hydroxytryptamine, the title compound is obtained.

EXAMPLE 30: N-{2-[5-(CYCLOHEXEN-3-YLOXY)INDOL-3-YL]-ETHYL}-CYCLOPROPYLCARBOXAMIDE $1.98 \times 10^{-2}$ mol of potassium carbonate, $1.33 \times 10^{-2}$ mol of N-[2-(5-hydroxyindol-3-yl)ethyl]cyclopropylcarboxamide dissolved in 20 cm³ of anhydrous acetone, and $2.1 \times 10^{-2}$ mol of 3-bromocyclohexene are introduced into a 50 cm³ flask with a ground neck. The mixture is heated under reflux for 22 hours. The reaction medium is filtered and the filtrate is evaporated under reduced pressure Recrystallisation of the evaporation residue in ethyl acetate yields purified N-{2-[5-(cyclohexen-3-yloxy)indol-3-yl]ethyl}-cyclopropylcarboxamide.

EXAMPLE 31: N-[2-(5-BENZYLOXYINDOL-3-YL)ETHYL]-CYCLOPROPYLCARBOXAMIDE 0.23 g of sodium is introduced in small portions, with magnetic stirring, into a 150 cm³ flask containing 50 cm³ of absolute ethanol. 0.01 mol of N-[2-(5-hydroxyindol-3-yl)ethyl]-cyclopropylcarboxamide is then added, stirring is continued for 30 minutes, and then the mixture is evaporated to dryness.

The resulting sodium compound is dissolved in 30 cm³ of anhydrous dimethylformamide. 0.011 mol of benzyl bromide is added, with magnetic stirring, by means of a dropping funnel.

The mixture is heated at 90° C. for 4 hours. The reaction medium is allowed to cool and is then poured onto ice. The resulting precipitate is suction filtered and washed with a 1N sodium hydroxide solution and then with water. The mixture is dried and recrystallised, yielding purified N-[2-(5-benzyloxyindol-3-yl)ethyl]-cyclopropylcarboxamide.

EXAMPLES 32 TO 37

Following the procedure of Example 18 but replacing propyl isocyanate with the appropriate isocyanates or isothiocyanate, the compounds of the following Examples are obtained:

EXAMPLE 32: N-[2 (5-METHOXYINDOL-3-YL)ETHYL]-N'-BENZYLUREA

EXAMPLE 33: N [2-(5-METHOXYINDOL-3-YL)ETHYL]-N'-CYCLOPROPYLUREA

EXAMPLE 34: N [2-(5-METHOXYINDOL-3-YL)ETHYL]-N'-CYCLOBUTYLUREA

EXAMPLE 35: N-[2 (5-METHOXYINDOL-3-YL)ETHYL]-N'-BUTYLUREA

EXAMPLE 36: N-[2 (5-METHOXYINDOL-3 YL)ETHYL]-N'-PROPYLTHIOUREA

EXAMPLE 37: N [2-(5-METHOXYINDOL-3-YL)ETHYL]-N'-CYCLOHEXYLTHIOUREA

EXAMPLES 38 AND 39

Following the procedure of Example 5 but replacing cyclopropanecarboxylic acid chloride with the appropriate acid chloride or acid anhydride, the compounds of the following Examples are obtained:

EXAMPLE 38: N-[2-(5-METHOXYBENZO[b]THIOPHEN-3-YL)ETHYL]-CYCLOBUTYLCARBOXAMIDE

EXAMPLE 39: N-[2 (5-METHOXYBENZO[b]THIOPHEN-3-YL)ETHYL]-CYCLOOCTYLCARBOXAMIDE

EXAMPLES 40 AND 41

Following the procedure of Example 19 but replacing propyl isocyanate with the appropriate isocyanate or isothiocyanate, the compounds of the following Examples are obtained:

EXAMPLE 40: N-[2-(5-METHOXYBENZO[b]THIOPHEN-3-YL)ETHYL]-N'-CYCLOPROPYLUREA

EXAMPLE 41: N-[2-(5-METHOXYBENZO[b]THIOPHEN 3-YL)ETHYL]-N'-CYCLOHEXYLTHIOUREA

EXAMPLES 42 AND 43

Following the procedure of Example 6 but replacing cyclopropanecarboxylic acid chloride with the appropriate acid chloride, the compounds of the following Examples are obtained:

EXAMPLE 42: N-[2-(6-CHLORO-5 METHOXYBENZO[b]THIOPHEN-3-YL)ETHYL]-CYCLOBUTYLCARBOXAMIDE

EXAMPLE 43: N-[2-(6-CHLORO-5-METHOXYBENZO[b]THIOPHEN-3-YL)ETHYL]-3-CYCLOPENTYLPROPIONAMIDE

EXAMPLES 44 TO 46

Following the procedure of Example 7 but replacing cyclopropanecarboxylic acid chloride with the appropriate acid chlorides, the compounds of the following examples are obtained:

EXAMPLE 44: N-[2-(BENZO[b]FURAN-3-YL)ETHYL]-CYCLOBUTYLCARBOXAMIDE

EXAMPLE 45: N-[2-(BENZO[b]FURAN-3-YL)ETHYL]-CYCLOHEXYLCARBOXAMIDE

EXAMPLE 46: N-[2 (BENZO[b]FURAN-3-YL)ETHYL]-TRIFLUOROACETAMIDE

EXAMPLES 47 TO 51

Following the procedure of Example 21 but replacing propyl isocyanate with the appropriate isocyanate or isothiocyanate, the compounds of the following Examples are obtained:

EXAMPLE 47: N-[2 (5 METHOXYBENZO[b]FURAN-3 YL)ETHYL]-N'-METHYLUREA

EXAMPLE 48: N-[2-(5 METHOXYBENZO[b]FURAN-3-YL)ETHYL]-N'-ETHYLUREA

EXAMPLE 49: N-[2-(5-METHOXYBENZO[b]FURAN-3-YL)ETHYL]-N'-HEXYLUREA

EXAMPLE 50: N-[2 (5 METHOXYBENZO[b]FURAN-3 YL)ETHYL]-N'-BENZYLUREA

EXAMPLE 51: N-[2 (5 METHOXYBENZO[b]FURAN-3-YL)ETHYL]-N'-PROPYLTHIOUREA

EXAMPLES 52 TO 54

Following the procedure of Example 11 but replacing cyclopropanecarboxylic acid chloride with the appropriate acid chloride, the compounds of the following Examples are obtained:

EXAMPLE 52: N-[2-(5-METHOXY 1,2-BENZISOXAZOL 3-YL)ETHYL]-ACETAMIDE

EXAMPLE 53: N-[2-(5-METHOXY-1,2-BENZISOXAZOL 3-YL)ETHYL]-BUTYRAMIDE

EXAMPLE 54: N-[2 (5 METHOXY-1,2-BENZISOXAZOL 3 YL)ETHYL]-3-CHLOROPROPIONAMIDE

EXAMPLES 55 AND 56

Following the procedure of Example 12 but replacing cyclopropanecarboxylic acid chloride with the appropriate acid chloride, the compounds of the following Examples are obtained:

EXAMPLE 55: N [2-(5-METHOXY-1,2-INDAZOL-3-YL)ETHYL]-ACETAMIDE

EXAMPLE 56: N-[2-(5-METHOXY-1,2-INDAZOL-3-YL)ETHYL]-PROPIONAMIDE

EXAMPLES 57 TO 60

Following the procedure of Example 9 but replacing cyclopropanecarboxylic acid chloride with the corresponding acid chloride, the compounds of the following Examples are obtained:

EXAMPLE 57: N-[2 (6-METHOXYBENZIMIDAZOL-1-YL)ETHYL]-ACETAMIDE

Melting point: 173°–175° C.

EXAMPLE 58: N-[2-(6-METHOXYBENZIMIDAZOL-1-YL)ETHYL]-BUTYRAMIDE

EXAMPLE 59: N-[2-(6-METHOXYBENZIMIDAZOL-1-YL)ETHYL]-PENTANAMIDE

EXAMPLE 60: N-[2-(6-METHOXYBENZIMIDAZOL-1-YL)ETHYL]2-BROMOACETAMIDE

EXAMPLES 61 TO 65

Following the procedure of Example 16 but replacing propyl isocyanate with the appropriate isocyanates or isothiocyanates, the compounds of the following Examples are obtained:

EXAMPLE 61: N-[2-(6-METHOXYBENZIMIDAZOL-1-YL)ETHYL]-N'-PROPYLUREA

EXAMPLE 62: N-[2-(6-METHOXYBENZIMIDAZOL-1-YL)ETHYL]-N'-BENZYLUREA

EXAMPLE 63: N-[2-(6-METHOXYBENZIMIDAZOL-1 YL)ETHYL]-N'-PROPYLTHIOUREA

EXAMPLE 64: N-[2-(6-METHOXYBENZIMIDAZOL-1-YL)ETHYL]-N'-CYCLOHEXYLTHIOUREA

EXAMPLE 65 : N-[2 (6-FLUORO-5-METHOXYINDOL-3-YL)ETHYL]-N'-PROPYLUREA

Melting point (dichloromethane-ether) 109°–110° C.

EXAMPLE A: DETERMINATION OF BINDING TO MELATONIN RECEPTORS

The binding of the compounds of the invention to melatonin receptors was carried out according to conventional methods on receptors of the pars tuberalis of sheep (Journal of Neuroendocrinology, Vol. 1, No. 1, pp. 1-4 (1989)).

The compounds of the invention bind in an extremely specific manner to the melatonin receptors with an affinity, for those exhibiting the most affinity, that is more than 100 times greater than that of melatonin itself. The compounds of the invention which were tested have a dissociation constant (Kd) of the order of $10^{-13}$ mol.$1^{-1}$, as compared with $6.3 \times 10^{-11}$ mol.$1^{-1}$ for melatonin itself.

EXAMPLE B: FOUR-PLATE TEST

The products of the invention are administered by the oesophageal route to groups of ten mice. One group receives gum syrup.

30 minutes after the administration of the products to be studied, the animals are placed in containers the floors of which comprise four metal plates. Each time the animal passes from one plate to another, it receives a slight electric shock (0.35 mA). The number of passages is recorded for a period of one minute. After administration, the compounds of the invention increase significantly the number of passages, which indicates the anxiolytic activity of the compounds of the invention.

EXAMPLE C: ACTIVITY OF THE PRODUCTS OF THE INVENTION ON ISCHAEMIC MICROCIRCULATION

The experimental study was carried out on the cremaster muscles of male rats (Sprague-Dawley) following ligature of the common iliac artery.

The muscles were placed in a transparent chamber and perfused with a solution of bicarbonate buffer equilibrated with a gaseous $CO_2/N_2$ mixture 5/95%. The velocity of the red corpuscles and the diameter of the first- or second-order arterioles irrigating the cremaster were measured, and the arterial blood flow was calculated. Identical information was obtained for four types of vessels.

The same type of measurement was carried out simultaneously:
on the cremaster perfused normally,
on the cremaster after ligature, that is to say the ischaematised cremaster, 2, 7, 14 and 21 days following ligature.

Two groups of animals were studied:
a control group without treatment,
a group treated p.o. with a product of the invention, at a dose of 0.1 mg.kg$^{-1}$ per day.

No difference was noted in either the velocity of the corpuscles or the diameter of the vessels in the normally irrigated cremaster muscles in the treated animals as compared with the controls.

On the other hand, at the level of the ischaematised cremaster muscle, the mean diameter of the arterioles was improved in the treated animals as compared with the controls. The velocity of the red corpuscles was normalised by treatment for 21 days.

In fact, in the treated animals, the velocity of the red corpuscles and the blood flow measured 7 days after ligature show no significant difference as compared with the values obtained in the non-ischaematised cremaster. These results are obtained without modification of the arterial pressure.

These results indicate that chronic treatment with one of the compounds of the invention improves microcirculation and blood irrigation of the ischaemic regions.

EXAMPLE D: STIMULATION OF IMMUNE RESPONSES

Red corpuscles of sheep were administered to groups of six mice. Those groups of mice were then treated subcutaneously with the compounds of the invention for a period of six days, and a control group was treated with a placebo. The mice are then left for four weeks and then received a repeat injection of red corpuscles of sheep without receiving further administrations of the product of the invention. The immune response was evaluated 3 days after the repeat injection. It is statistically increased in the group treated with the compounds of the invention.

EXAMPLE E: INHIBITION OF OVULATION

Adult female rats with regular four-day cycles are used. Vaginal smears were taken daily, and rats were selected after they had exhibited at least two consecutive four-day cycles.

Each cycle is composed of two days of dioestrus, one day of pro-oestrus and one day of oestrus.

On the afternoon of the day of pro-oestrus, luteinizing hormone is released into the blood by the hypophysis.

This hormone induces ovulation, which is indicated by the presence of eggs at the oviduct on the day of oestrus.

The compounds of the invention are administered orally at midday on the day of oestrus. The treated rats and the controls are sacrificed on the day of oestrus. The oviducts are examined. A significant percentage reduction in the number of eggs in the oviducts of rats treated with the compounds of the invention is noted.

EXAMPLE F: PHARMACEUTICAL COMPOSITION Tablets containing 5 mg of N-[2-(5-METHOXYINDOL-3-YL)ETHYL]-N'-PROPYLUREA Preparation formulation for 1000 tablets:

| | |
|---|---|
| N-[2-(5-methoxyindol-3-yl)ethyl]-N'-propylurea | 5 g |
| wheat starch | 20 g |
| corn starch | 20 g |
| lactose | 30 g |
| magnesium stearate | 2 g |
| silica | 1 g |
| hydroxypropylcellulose | 2 g |

We claim:

1. A compound selected from those of the formula (I):

in which:

Ar' represents:

benzo[b]furan-3-yl of formula (V):

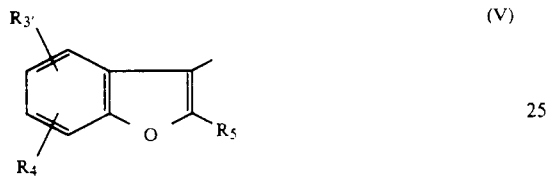

$R_1$ represents:

a group

in which $R_7$ represents unsubstituted or optionally substituted cycloalkyl, unsubstituted or optionally substituted cycloalkyl-($C_1$-$C_4$)alkyl, or trifluoromethyl, a group

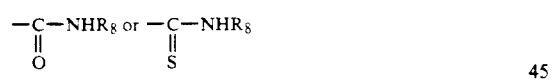

in which $R_8$ represents linear or branched lower alkyl having 1 to 6 carbon atoms, inclusive, unsubstituted of optionally substituted cycloalkyl, unsubstituted or optionally substituted cycloalkyl-($C_1$-$C_4$) alkyl unsubstituted or optionally substituted aryl, or unsubstituted or optionally substituted arylalkyl in which the alkyl chain contains 1 to 3 carbon atoms, inclusive, or a group

in which n represents 1 to 3 inclusive and $E_1$ represents a radical selected from:

morpholino and piperazine which radical is unsubstituted or substituted by a radical —$(CH_2)_{n'}$-$E_2$ wherein n' represents an integer 1 to 4 inclusive and $E_2$ represents phenyl or naphthyl, each of which is unsubstituted or substituted by 1 to 3 radicals selected from: halogen, ($C_1$-$C_4$)alkyl, and ($C_1$-$C_4$)alkoxy;

$R_2$ represents hydrogen or linear or branched lower alkyl having 1 to 6 carbon atoms inclusive;

$R_3$ represents hydrogen, linear or branched lower alkyl having 1 to 6 carbon atoms, inclusive unsubstituted or optionally substituted aryl, unsubstituted or optionally substituted arylalkyl or diarylalkyl in which the alkyl chain contains 1 to 3 carbon atoms, inclusive, or cycloalkyl or cycloalkylalkyl in which the alkyl chain contains 1 to 3 carbon atoms, inclusive, $R_3'$ represents hydrogen or a group —O—$R_3$ wherein $R_3$ is as defined above;

$R_4$ represents hydrogen, halogen, hydroxy, linear or branched alkoxy having 1 to 6 carbon atoms, inclusive, or linear or branched lower alkyl having 1 to 6 carbon atoms, inclusive, $R_5$ represents hydrogen, halogen, linear or branched lower alkyl having 1 to 6 carbon atoms, inclusive, unsubstituted or optionally substituted phenyl, or unsubstituted or optionally substituted phenylaklyl in which the alkyl chain contains 1 to 3 carbon atoms, inclusive, and $R_6$ represents hydrogen, or linear or branched lower alkyl having from 1 to 6 carbon atoms, inclusive;

an optical isomer, and an addition salt thereof with a pharmaceutically-acceptable acid or base, with the proviso that:

Ar' may not represent 7-methoxybenzo[b]furan-3-yl when $R_1$ represents cyclopropylcarbonyl;

and wherein the term "substituted" associated with the expressions "aryl", "arylalkyl", "diarylalkyl", "phenyl" and "phenylalkyl" means that the aromatic nucleus or nuclei may be substituted by one or more radicals selected from: linear or branched lower alkyl having 1 to 6 carbon atoms, inclusive, linear or branched lower alkoxy having from 1 to 6 carbon atoms, inclusive, hydroxy, halogen, nitro, and trifluoromethyl;

the term "substituted" associated with the expressions "cycloalkyl" and "cycloalkyl-($C_1$-$C_4$ )alkyl" means that the cyclic system may be substituted by one or more radicals selected from: halogen, linear or branched lower alkyl having 1 to 6 carbon atoms, inclusive, and linear or branched lower alkoxy having 1 to 6 carbon atoms, inclusive;

the term "cycloalkyl" designates a saturated or unsaturated cyclic system having 3 to 8 carbon atoms, inclusive, and the expression "aryl group" means pyridyl, phenyl, naphthyl, thienyl, furyl, or pyrimidyl.

2. A compound according to claim 1 selected from those in which Ar' represents a benzo[b]furan-3-yl radical, which corresponds to one of the benzo[b]furans of formula:

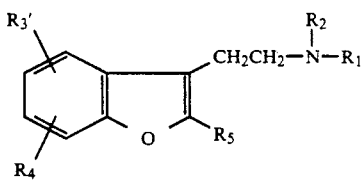

in which $R_1$, $R_2$, $R'_3$ $R_4$ and $R_5$ have the same meaning as in claim 1, an optical isomer, and an addition salt thereof with a pharmaceutically-acceptable acid or base.

3. A compound according to claim 1 which is N-[2-(5-methoxybenzo[b]furan-3yl)ethyl]-N'-propylurea.

4. A pharmaceutical composition useful in treating or in preventing a disorder of the melatoninergic system containing as active principle an effective amount of a compound as claimed in claim 1, in combination with one or more pharmaceutically-acceptable excipients or vehicles.

5. A method of treating a mammal afflicted with a disorder of the melatoninergic system comprising the step of administering to the said mammal an amount of a compound as claimed in claim 1 which is effective for alleviation of said disorder.

* * * * *

UNITED STATES PATENT AND TRADEMARK OFFICE
CERTIFICATE OF CORRECTION

PATENT NO. : 5,308,866

DATED : May 3, 1994

INVENTOR(S) : Daniel Lesieur, Said Yous, Patrick Depreux, Jean-Andrieux, Gérard Adam, Daniel H. Caignard, Béatrice Guardiola It is certified that error appears in the above-indentified patent and that said Letters Patent is hereby corrected as shown below:

```
Column 3, line 28; "from I" should read -- from 1 --.
Column 5, line 42; and Column 6, line 7; in each
     instance, a total of 2, "I₆₈):" should read --(Iϵ): --.
Column 5, line 56; "I₆₈'):" should read --(Iϵ'): --.
Column 8, line 56; "EXAMPLE 7 N [2-(5" should read
     -- EXAMPLE 7:  N-[2-(5- --.
Column 8, line 63; "-111-1" should read -- -1111 --.
Column 9, approximately line 27; "N-2-(6-" should read
     -- N-[2-(6- --.
Column 9, approximately line 27, at the end of the line;
     "-1" should read -- -1- --.
Column 9, line 38; "N [2" should read -- N-[2- --.
Column 9, line 47; "N [2" should read -- N-[2- --.
Column 9, line 51; "5methoxytryptamine" should read
     -- 5-methoxytryptamine --.
Column 9, line 52; "24(4}pp." should read --24 (4) pp. --.
Column 9, approximately line 56; [2-(5" should read
     --[2-(5- --.
Column 9, approximately line 65; "[2 (5-" should read
     -- [2-(5- --
Column 10, line 50; "16: N" should read --16: N- --.
Column 10, line 61; "-1,2" should read -- -1,2- --.
Column 11, line 30; "N-[2" should read -- N-[2- --.
Column 11, line 31; "THIOPHEN-3" should read --
     -- THIOPHEN-3- --.
Column 11, line 40; "N [2-(6-CHLORO-5" should read
     -- N-[2-(6-CHLORO-5- --.
Column 11, line 64; "N [2" should read --N-[2- --.
```

UNITED STATES PATENT AND TRADEMARK OFFICE
CERTIFICATE OF CORRECTION

PATENT NO. : 5,308,866       Page 2 of 4

DATED : May 3, 1994

INVENTOR(S) : Daniel Lesieur, Said Yous, Patrick Depreux, Jean Andrieux, Gérard Adam, Daniel H.Caignard, Béatrice Guardiola It is certified that error appears in the above-indentified patent and that said Letters Patent is hereby corrected as shown below:

```
Column 12, line 8;  "N [2-(5" should read -- N-[2-(5- --.
Column 13, line 41; "(5 METHOXYINDOL" should read --
    -- (5-METHOXYINDOL- --.
Column 13, line 45; "N-[2 (5" should read -- N-[2-(5- --.
Column 13, line 47; "PIPERAZIN-1" should read --
    -- PIPERAZIN-1- --.
Column 13, line 67; "pressure Recrystallisation" should read
    -- pressure. Recrystallisation --.
Column 14, line 34; "N" at the end of the line, should read
    -- N- --.
Column 14, line 38; "N" at the end of the line, should read
    -- N- --.
Column 14, line 42; "N-[2"  should read -- N-[2- --.
Column 14, line 45; "N-[2 (5-" should read -- N-[2-(5- --.
Column 14, approximately line 48; "EXAMPLE 37:N" should read
    -- EXAMPLE 37: N- --.
Column 14, line 60; "N-[2" should read -- N-[2- --.
Column 15, line 6;  "insert a hyphen "-" after "THIOPHEN".
Column 15, line 15; "CHLORO-5" should read -- CHLORO-5- --.
Column 15, line 46; "N-[2 (5" should read  --N-[2-(5- --.
Column 15, line 47; insert a hyphen "-" after "FURAN-3".
Column 15, line 50; insert a hyphen "-" after "N-[2-(5".
Column 15, line 57; insert a hyphen "-" after "(5" and
    after "2".
Column 15, line 58; insert a hyphen "-" after "FURAN-3".
Column 15, line 60; insert a hyphen "-" after "(5" and
    after "2".
Column 16, line 1; insert a hyphen "-" after "METHOXY".
Column 16, line 3; insert a hyphen "-" after "BENZISOXAZOL".
Column 16, line 8; insert a hyphen "-" after "BENZISOXAZOL".
Column 16, line 12; insert a hyphen "-" after "(5".
Column 16, line 13; insert a hyphen "-" after "3".
```

UNITED STATES PATENT AND TRADEMARK OFFICE
CERTIFICATE OF CORRECTION

PATENT NO. : 5,308,866

DATED : May 3, 1994

INVENTOR(S) : Daniel Lesieur, Said Yous, Patrick Depreux, Jean Andrieux, Gérard Adam, Daniel H. Caignard, Béatrice Guardiola It is certified that error appears in the above-indentified patent and that said Letters Patent is hereby corrected as shown below:

Column 16, line 24; approximately line 24;
    insert a hyphen "-" after "N".
Column 16, approximately line 42; insert a hyphen "-" after "2".
Column 16, approximately line 50; move the "E" at the end of
    line 49 to the beginning of line 50 and insert before
    "THYL"
Column 16, line 54; move the "E" at the end of line 54 to the
    beginning of line 55 and insert before "THYL".
Column 16, line 59; move the "E" at the end of line 59 to the
    beginning of line 60 and insert before "THYL".
Column 17, line 2; move the "E" at the end of line 2 to the
    beginning of line 3 and insert before "THYL".
Column 17, line 6; move the "E" at the end of line 6 to the
    beginning of line 7 and insert before "THYL".
Column 17, line 9; insert a hyphen "-" after "1".
Column 17, approximately line 13; move the "E" at the end of
    line 13 to the beginning of line 14 and insert before
    "THYL".
Column 17, approximately line 15; insert a hyphen at the end of
    line 15 after "[2".
Column 19, approximately line 49; "substituted of" should read
    -- substituted or --.
Column 19, line 66; "piperazine which" should read
    -- piperazine, which --.
Column 19, line 68; "represents an integer 1 to 4" should read
    -- represents 1 to 4 --.

UNITED STATES PATENT AND TRADEMARK OFFICE
CERTIFICATE OF CORRECTION

PATENT NO. : 5,308,866

DATED : May 3, 1994

INVENTOR(S) : Daniel Lesieur, Said Yous, Patrick Depreux, Jean Andrieux, Gérard Adam, Daniel H. Caignard, Béatrice Guardiola It is certified that error appears in the above-indentified patent and that said Letters Patent is hereby corrected as shown below:

Column 20, line 3; "cals selected" should read
    -- cals inclusive selected --.
Column 20, line 31; delete "from".
Column 22, line 2; "3yl)" should read -- 3-yl) --.

Signed and Sealed this

Eighteenth Day of October, 1994

Attest:

BRUCE LEHMAN

Attesting Officer       Commissioner of Patents and Trademarks